US010117763B2

(12) United States Patent
Fleury et al.

(10) Patent No.: US 10,117,763 B2
(45) Date of Patent: Nov. 6, 2018

(54) REDUCED GRANULATION AND INFLAMMATION STENT DESIGN

(71) Applicant: Boston Scientific Scimed, Inc., Maple Grove, MN (US)

(72) Inventors: Sean P. Fleury, Brighton, MA (US); Dane T. Seddon, Boston, MA (US); Barry Weitzner, Acton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 459 days.

(21) Appl. No.: 14/660,468

(22) Filed: Mar. 17, 2015

(65) Prior Publication Data

US 2015/0265437 A1    Sep. 24, 2015

Related U.S. Application Data

(60) Provisional application No. 61/954,786, filed on Mar. 18, 2014.

(51) Int. Cl.
*A61F 2/89*    (2013.01)
*A61F 2/915*    (2013.01)
*A61F 2/82*    (2013.01)

(52) U.S. Cl.
CPC ............... *A61F 2/89* (2013.01); *A61F 2/915* (2013.01); *A61F 2002/825* (2013.01); *A61F 2002/91525* (2013.01); *A61F 2002/91575* (2013.01); *A61F 2250/0018* (2013.01); *A61F 2250/0036* (2013.01)

(58) Field of Classification Search
CPC ...... A61F 2/91; A61F 2/915; A61F 2002/068; A61F 2002/823; A61F 2002/91575; A61F 2/06; A61F 2/07; A61F 2/89; A61F 2002/9155; A61F 2002/91516; A61F 2002/821; A61F 2002/91525; A61F 2002/91558
See application file for complete search history.

(56) References Cited

U.S. PATENT DOCUMENTS

| 4,994,071 | A | 2/1991 | MacGragor |
| 5,104,404 | A | 4/1992 | Wolff |
| 5,383,892 | A | 1/1995 | Cardon et al. |

(Continued)

FOREIGN PATENT DOCUMENTS

| CA | 2619429 A1 | 3/2007 |
| CN | 203408130 | 1/2014 |

(Continued)

*Primary Examiner* — Seema Mathew
(74) *Attorney, Agent, or Firm* — Seager, Tufte & Wickhem, LLP

(57) ABSTRACT

A stent of the present disclosure has a variable radial force along the longitudinal length of the stent. In particular, the radial force of the center is greater than the radial force of the ends of the stent. Without being bound by theory, the radial force is affected by the strut angle θ, the wall thickness t, the number of strut pairs, and combinations thereof. In one aspect of the present disclosure, the stent has a variable strut angle θ, a variable wall thickness t, and a variable number of strut pairs. By adjusting the strut angle θ, the wall thickness t, and the number of strut pairs of the serpentine bands, the stent will have a variable radial force without the need for additional processing steps.

18 Claims, 7 Drawing Sheets

(56) References Cited

U.S. PATENT DOCUMENTS

| | | | |
|---|---|---|---|
| 5,449,373 A | 9/1995 | Pinchasik et al. | |
| 5,674,277 A | 10/1997 | Freitag | |
| 5,716,396 A | 2/1998 | Williams, Jr. | |
| 5,741,327 A | 4/1998 | Frantzen | |
| 5,807,404 A | 9/1998 | Richter | |
| 5,810,872 A | 9/1998 | Kanesaka et al. | |
| 5,814,063 A | 9/1998 | Freitag | |
| 5,836,966 A | 11/1998 | St. Germain | |
| 5,843,175 A | 12/1998 | Frantzen | |
| 5,913,895 A | 6/1999 | Burpee et al. | |
| 5,925,061 A | 7/1999 | Ogi et al. | |
| 5,938,697 A * | 8/1999 | Killion | A61F 2/91 623/1.15 |
| 5,954,743 A | 9/1999 | Jang | |
| 6,017,365 A | 1/2000 | Von Oepen | |
| 6,022,374 A | 2/2000 | Imran | |
| 6,039,756 A | 3/2000 | Jang | |
| 6,042,597 A | 3/2000 | Kveen et al. | |
| 6,190,406 B1 | 2/2001 | Duerig et al. | |
| 6,210,429 B1 | 4/2001 | Vardi et al. | |
| 6,348,065 B1 | 2/2002 | Brown et al. | |
| 6,352,552 B1 | 3/2002 | Levinson et al. | |
| 6,423,091 B1 | 7/2002 | Hojeibane | |
| 6,492,615 B1 | 12/2002 | Flanagan | |
| 6,602,281 B1 | 8/2003 | Klein | |
| 6,743,252 B1 | 6/2004 | Bates et al. | |
| 6,878,162 B2 | 4/2005 | Bales et al. | |
| 6,899,729 B1 * | 5/2005 | Cox | A61F 2/915 606/200 |
| 6,923,829 B2 | 8/2005 | Boyle et al. | |
| 6,945,993 B2 | 9/2005 | Kveen et al. | |
| 6,949,120 B2 | 9/2005 | Kveen et al. | |
| 6,962,604 B2 | 11/2005 | Hijlkema | |
| 7,131,993 B2 | 11/2006 | Gregorich | |
| 7,527,644 B2 | 5/2009 | Mangiardi et al. | |
| 7,547,321 B2 | 6/2009 | Silvestri et al. | |
| 7,556,644 B2 | 7/2009 | Burpee et al. | |
| 7,604,660 B2 | 10/2009 | Borg et al. | |
| 7,608,099 B2 | 10/2009 | Johnson et al. | |
| 7,637,934 B2 | 12/2009 | Mangiardi et al. | |
| 7,637,942 B2 | 12/2009 | Mangiardi et al. | |
| 7,651,520 B2 | 1/2010 | Fischell et al. | |
| 7,731,654 B2 | 6/2010 | Mangiardi et al. | |
| 7,785,360 B2 | 8/2010 | Freitag | |
| 7,803,180 B2 | 9/2010 | Burpee et al. | |
| 7,806,918 B2 | 10/2010 | Nissl et al. | |
| 7,875,068 B2 | 1/2011 | Mangiardi et al. | |
| 7,887,579 B2 | 2/2011 | Mangiardi et al. | |
| 7,942,921 B2 | 5/2011 | Nissl et al. | |
| 7,959,671 B2 | 6/2011 | Mangiardi et al. | |
| 8,080,053 B2 | 12/2011 | Satasiya et al. | |
| 8,128,679 B2 | 3/2012 | Casey | |
| 8,142,488 B2 | 3/2012 | Reynolds et al. | |
| 8,206,436 B2 | 6/2012 | Mangiardi et al. | |
| 8,262,721 B2 | 9/2012 | Welborn et al. | |
| 8,267,987 B2 | 9/2012 | Johnson et al. | |
| 8,298,277 B2 | 10/2012 | Mangiardi et al. | |
| 8,323,350 B2 | 12/2012 | Nissl | |
| 8,353,946 B2 | 1/2013 | Mangiardi et al. | |
| 8,535,366 B2 | 9/2013 | Mangiardi et al. | |
| 8,628,563 B2 * | 1/2014 | Fliedner | A61F 2/91 623/1.15 |
| 8,652,196 B2 | 2/2014 | Nissl | |
| 8,663,313 B2 * | 3/2014 | Boismier | A61F 2/915 623/1.15 |
| 8,834,558 B2 | 9/2014 | Nissl | |
| 8,926,683 B2 | 1/2015 | Gill et al. | |
| 2001/0004705 A1 | 6/2001 | Killion et al. | |
| 2004/0044400 A1 | 3/2004 | Cheng et al. | |
| 2004/0088044 A1 | 5/2004 | Brown et al. | |
| 2004/0215325 A1 | 10/2004 | Penn et al. | |
| 2004/0230293 A1 | 11/2004 | Yip et al. | |
| 2004/0243216 A1 | 12/2004 | Gregorich | |
| 2005/0015136 A1 | 1/2005 | Ikeuchi et al. | |
| 2005/0085899 A1 | 4/2005 | Thornton | |
| 2005/0131515 A1 | 6/2005 | Cully et al. | |
| 2007/0005127 A1 | 1/2007 | Boekstegers et al. | |
| 2007/0213810 A1 | 9/2007 | Newhauser et al. | |
| 2008/0215133 A1 | 9/2008 | Richter | |
| 2008/0221664 A1 | 9/2008 | Bales et al. | |
| 2009/0118810 A1 | 5/2009 | Klein et al. | |
| 2009/0187240 A1 | 7/2009 | Clerc et al. | |
| 2009/0228088 A1 * | 9/2009 | Lowe | A61F 2/91 623/1.2 |
| 2009/0248132 A1 | 10/2009 | Bloom et al. | |
| 2010/0274348 A1 * | 10/2010 | Schaffner | A61F 2/91 623/1.16 |
| 2012/0116498 A1 * | 5/2012 | Chuter | A61F 2/2412 623/1.26 |
| 2012/0150277 A1 | 6/2012 | Wood et al. | |
| 2012/0303112 A1 * | 11/2012 | Armstrong | A61F 2/07 623/1.16 |
| 2012/0310363 A1 | 12/2012 | Gill et al. | |
| 2013/0018215 A1 | 1/2013 | Snider et al. | |
| 2013/0018452 A1 | 1/2013 | Weitzner et al. | |
| 2013/0085565 A1 | 4/2013 | Eller et al. | |
| 2013/0103163 A1 | 4/2013 | Krimsky et al. | |
| 2013/0110253 A1 | 5/2013 | Gill et al. | |
| 2013/0116770 A1 | 5/2013 | Robinson | |
| 2013/0116771 A1 | 5/2013 | Robinson | |
| 2013/0116772 A1 | 5/2013 | Robinson | |
| 2013/0123897 A1 | 5/2013 | Robinson | |
| 2013/0172983 A1 | 7/2013 | Clerc et al. | |
| 2013/0184808 A1 | 7/2013 | Hall et al. | |
| 2013/0184810 A1 | 7/2013 | Hall et al. | |
| 2013/0325141 A1 | 12/2013 | Gill et al. | |
| 2014/0067047 A1 | 3/2014 | Eller et al. | |
| 2014/0079758 A1 | 3/2014 | Hall et al. | |
| 2014/0081414 A1 | 3/2014 | Hall et al. | |
| 2014/0086971 A1 | 3/2014 | Hall et al. | |
| 2014/0248418 A1 | 9/2014 | Eller et al. | |
| 2014/0249619 A1 | 9/2014 | Eller et al. | |
| 2014/0257461 A1 | 9/2014 | Robinson et al. | |
| 2014/0277573 A1 | 9/2014 | Gill et al. | |
| 2015/0073529 A1 | 3/2015 | Fleury et al. | |
| 2016/0278951 A1 * | 9/2016 | Dagan | A61F 2/915 |
| 2018/0104054 A1 * | 4/2018 | Chuter | A61F 2/2412 |

FOREIGN PATENT DOCUMENTS

| | | |
|---|---|---|
| EP | 0732088 A2 | 9/1996 |
| EP | 950386 A2 | 10/1999 |
| EP | 951877 A2 | 10/1999 |
| JP | 2002500533 A | 1/2002 |
| JP | 2002355315 A | 12/2002 |
| JP | 2003532441 A | 11/2003 |
| JP | 2007500051 A | 1/2007 |
| WO | 2000016718 A1 | 3/2000 |
| WO | 0071053 A1 | 11/2000 |

* cited by examiner

REDUCED GRANULATION AND INFLAMMATION STENT DESIGN

CROSS-REFERENCE TO RELATED APPLICATIONS

The present application claims priority to U.S. Application No. 61/954,786 filed Mar. 18, 2014, the content of which is incorporated by reference in its entirety.

BACKGROUND

A stent is a medical device introduced to a body lumen. Conventionally, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, gastrointestinal tract, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

All US patents and applications and all other published documents mentioned anywhere in this application are incorporated herein by reference in their entirety.

Without limiting the scope of the present disclosure, a brief summary of some of the claimed embodiments is set forth below. Additional details of the summarized embodiments of the present disclosure and/or additional embodiments of the present disclosure may be found in the Detailed Description of the Invention below. A brief abstract of the technical disclosure in the specification is also provided. The abstract is not intended to be used for interpreting the scope of the claims.

SUMMARY

In at least one embodiment, the stent has a radial force that varies along the longitudinal length of the stent. In some embodiments, the stent has a variable strut angle, a variable wall thickness, and a variable number of strut pairs.

In one aspect, a stent has a longitudinal length, a radial force that varies along the longitudinal length, and interconnected serpentine bands, each serpentine band comprises struts interconnected by proximal turns and distal turns, each serpentine band has a strut angle, a number of strut pairs, and a wall thickness, the serpentine bands comprise a first serpentine band having a first radial force and a second serpentine band having a second radial force less than the first radial force, wherein: the strut angle of the first serpentine band is less than the strut angle of the second serpentine band; the number of strut pairs of the first serpentine band is greater than the number of strut pairs of second serpentine band; and the wall thickness of the first serpentine band is greater than the wall thickness of the second serpentine band.

In a further aspect of the stent, the first serpentine band is positioned between two second serpentine bands, each second serpentine band forms an end of the stent, and the radial force gradually decreases from the first radial force of the first serpentine band to the second radial force of the second serpentine bands at each end of the stent.

In a further aspect of the stent, the first serpentine bands are a plurality of serpentine bands forming a center region of the stent, and the second serpentine bands are a plurality of serpentine bands forming a first end region and a second end region of the stent, the center region is positioned between the first and second end regions, the first and second end regions have a lower radial force than the center region.

In a further aspect of the stent, the serpentine bands further comprise a third serpentine band positioned between the first and second serpentine bands, the third serpentine band having a third radial force less than the first radial force and greater than the second radial force, wherein: the strut angle of the third serpentine band is greater than the strut angle of the first serpentine band and less than the strut angle of the second serpentine band; the number of strut pairs of the third serpentine band is less than the number of strut pairs of the first serpentine band and greater than the number of strut pairs of the first serpentine band; and the wall thickness of the third serpentine band is less than the wall thickness of the first serpentine band, and greater than the wall thickness of the second serpentine band.

In a further aspect of the stent, the third serpentine band is a plurality of third serpentine bands forming transition regions positioned between the center region and each end region, wherein for the third serpentine bands: the strut angle decreases from the center region to the end region; the number of strut pairs decreases from the center region to the end region; and the wall thickness decreases from the center region to the end region.

In a further aspect of the stent, for the first serpentine band: the strut angle is fifteen times smaller than the strut angle of the second serpentine band; the number of strut pairs is twice the number of strut pairs of the second serpentine band; and the wall thickness is 1.5 to 4 times larger than the wall thickness of the second serpentine band.

In a further aspect of the stent, the struts have a strut length and a strut width, further wherein for the first serpentine band: the strut length is greater than the strut length of the second serpentine band; and the strut width is greater than the strut width of the second serpentine band.

In a further aspect of the stent, each second serpentine band is engaged to a first serpentine band by longitudinal connectors and adjacent first serpentine bands are engaged by circumferential connectors.

In a further aspect of the stent, each longitudinal connector engages one proximal turn and one distal turn, and each circumferential connector engages two proximal turns.

In a further aspect of the stent, each circumferential connector comprises a straight longitudinal segment, a first curved segment, a circumferential segment, and a second curved segment, the straight longitudinal segment being positioned between two struts of a first serpentine band.

In a further aspect of the stent, an orientation of the circumferential connectors engaging two serpentine center bands is the same but alternates between two opposite orientations along the longitudinal length of the stent.

In a further aspect of the stent, the circumferential segment is configured to extend outward from a stent envelope defined by the first serpentine band when the stent is in a true expanded state.

In a further aspect of the stent, the struts are straight.

In a further aspect of the stent, the struts of the center region are at an angle relative to the longitudinal axis of the stent, and the struts of the end regions are parallel to the longitudinal axis of the stent.

In a further aspect of the stent, each serpentine band has a uniform strut angle.

In another aspect, a stent with a variable radial force comprises: a first serpentine band comprising struts interconnected by proximal turns and distal turns, a first strut angle, a first number of strut pairs, and a first wall thickness; and a second serpentine band comprising struts interconnected by proximal turns and distal turns, a second strut angle less than the first strut angle, a second number of strut pairs greater than the first number of strut pairs, and a second wall thickness greater than the first wall thickness.

In a further aspect of the stent, the first serpentine band is two serpentine end bands, one of the two serpentine end bands forms one end of the stent and the other of the two serpentine end bands forms the other end of the stent, the second serpentine band being a plurality of serpentine center bands positioned between the two serpentine end bands.

In a further aspect of the stent, one of the two serpentine end bands is engaged to one of the plurality of serpentine center bands by a first plurality of longitudinal connectors; and the other serpentine end band is engaged to another of the plurality of serpentine center bands by a second plurality of longitudinal connectors; and pairs of serpentine center bands being engaged by a plurality of circumferential connectors.

In a further aspect of the stent, the second number of strut pairs is twice the first number of strut pairs; the first strut angle is 15 times larger than the second strut angle; and the first wall thickness is 1.5 to 4 times greater than the second wall thickness.

In a further aspect of the stent, the struts of the first serpentine bands have a first strut length and a first strut width; the struts of second serpentine bands have a second strut length and a second strut width; wherein the second strut length is greater than the first strut length, and the second strut width is greater than the first strut width.

In yet another aspect, a stent comprises: a first serpentine end band forms a first end of the stent, and a second serpentine end band forms a second end of the stent, each serpentine end band comprises struts interconnected by proximal turns and distal turns, an end band number of strut pairs, an end band strut angle, and an end band thickness; serpentine center bands comprise center struts interconnected by proximal turns and distal turns, a center band number of strut pairs greater than the end band number of strut pairs, a center band strut angle less than the end band strut angle, and a center band thickness greater than the end band thickness; circumferential connectors engage proximal turns of adjacent center serpentine bands; a first plurality of longitudinal connectors engage one of the center serpentine bands to the first serpentine end band; and a second plurality of longitudinal connectors engage another of the center serpentine bands to the second serpentine end band.

In a further aspect of the stent, each serpentine end band and each serpentine center band comprise proximal turns and distal turns, wherein each longitudinal connector engages one proximal turn and one distal turn, and each circumferential connector engages two proximal turns.

In a further aspect of the stent, the end band number of strut pairs is nine strut pairs, and the end band strut angle is 1.76 degrees; the end band thickness is 0.0130 mm; the center band number is eighteen strut pairs, the center band strut angle is 0.120 degrees; and the center band thickness is 0.0130 mm.

In a further aspect of the stent, the center struts are at an angle relative to the longitudinal axis of the stent, and the end struts are parallel to the longitudinal axis of the stent.

In a further aspect of the stent, each end strut is positioned a first distance from one adjacent end strut and a second distance from another adjacent end strut, the second distance being greater than the first distance.

These and other embodiments are pointed out with particularity in the claims annexed hereto and forming a part hereof. However, for further understanding reference can be made to the drawings which form a further part hereof and the accompanying descriptive matter, in which one or more embodiments are illustrated and described.

BRIEF DESCRIPTION OF THE DRAWING(S)

DETAILED DESCRIPTION

Figure 1:
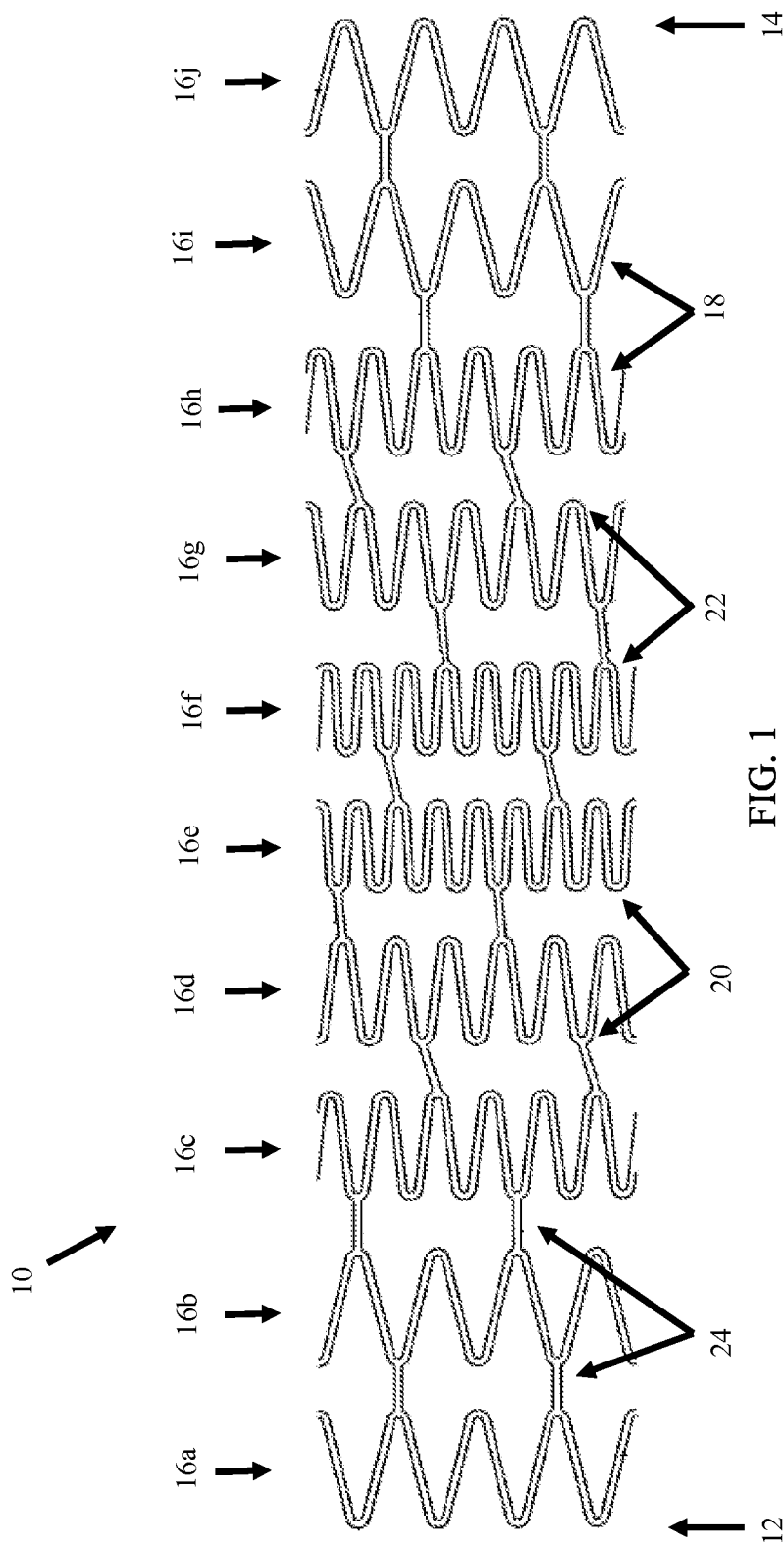
FIG. 1 is a flat plan view of an exemplary stent pattern in a non-expanded state.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

When implanted in a body lumen, the stent creates patency in the body lumen with radial force. As used in this disclosure, "radial force" is an amount of outward radial force applied by the stent against a lumen wall when the stent is implanted in a body lumen. Thus, a stent needs a certain amount of radial force in order to open a stricture when placed in a lumen to maintain patency. However, if the pressure by the stent on the lumen wall is great enough, the tissue can activate inflammatory macrophages and, once the inflammatory macrophages are activated, the affected region usually is not limited to a pinpoint area but instead is an extended zone. If the radial force is too great, excessive inflammation that induces swelling and granulation of tissue can occur. It is an object of the stent of the present disclosure to minimize or eliminate swelling and granulation of tissue when the stent is implanted in a body lumen.

A stent 10 of the present disclosure is tubular and has a variable radial force along the longitudinal length L of the stent. In particular, the radial force of the center is greater than the radial force of the ends of the stent.

The stent has one center region and two end regions. As used in this application, a "region" is a section of the tubular stent that extends from a first longitudinal position to a second longitudinal position, extends around the entire circumference of the tubular stent, and includes at least one serpentine band 16. In a further aspect, the stent has a transition region positioned between the center region and an end region. The stent can have one or two transition regions. Hereinafter, serpentine bands forming a center region are referred to as serpentine center bands; serpentine bands forming a transition region are referred to as serpentine transition bands; and serpentine bands forming an end region are referred to as serpentine end bands.

Each serpentine band 16 is formed of struts 18 interconnected by turns 20, 22 facing opposite directions. As used in this disclosure, a "serpentine band" extends around the entire circumference of the stent so that the struts and turns form a closed pathway. Each turn is engaged to two struts and each strut is engaged to two turns facing opposite directions. A length of the strut (hereinafter strut length 19) is measured between the two oppositely facing turns. The struts can be straight or have at least one bend. Further, the struts can extend parallel to the longitudinal axis of the stent, or extend at an oblique angle to the longitudinal axis of the stent. As used herein, an "oblique angle" relative to the longitudinal axis is neither perpendicular nor parallel to the longitudinal axis. Further the struts can have a uniform strut length or different strut lengths. As used herein, "uniform" means the same. For example, if struts of a serpentine band have a uniform length, then all the struts have the same length.

Each serpentine band has a longitudinal band length and is spaced longitudinally apart from at least one other serpentine band by a longitudinal spacing length s. Connectors 24 engage adjacent serpentine bands. The connectors can be straight; have at least one bend; extend longitudinally; and/or extend circumferentially. As used herein, a "circumferential connector" has ends that are circumferentially offset, while a "longitudinal connector" has ends that are circumferentially aligned. Each connector extends from a turn of one serpentine band to a turn of a longitudinally adjacent serpentine band. The turns engaged by a connector can be facing in opposite directions or in the same direction.

Without being bound by theory, the radial force of the serpentine bands is affected by the strut angle $\theta$, the wall thickness t, the number of strut pairs, and combinations thereof. In one aspect, the serpentine bands of the stent have a variable strut angle $\theta$, a variable wall thickness t, and a variable number of strut pairs. By adjusting the strut angle $\theta$, the wall thickness t, and/or the number of strut pairs of the serpentine bands, the stent will have a variable radial force without the need for additional processing steps.

Figure 2:
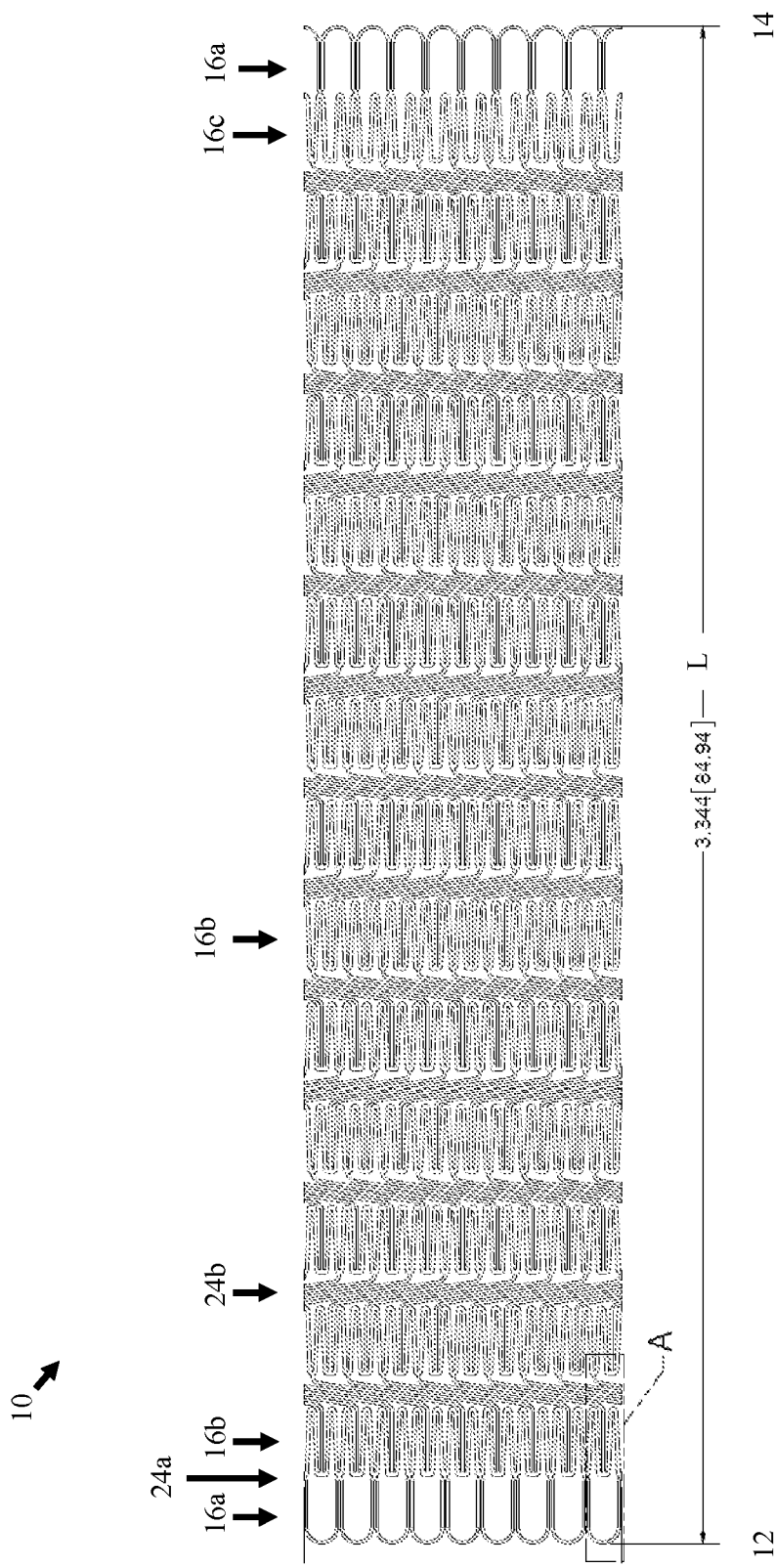
FIG. 2 is a flat plan view of an exemplary stent pattern in a non-expanded state.
Figure 4:
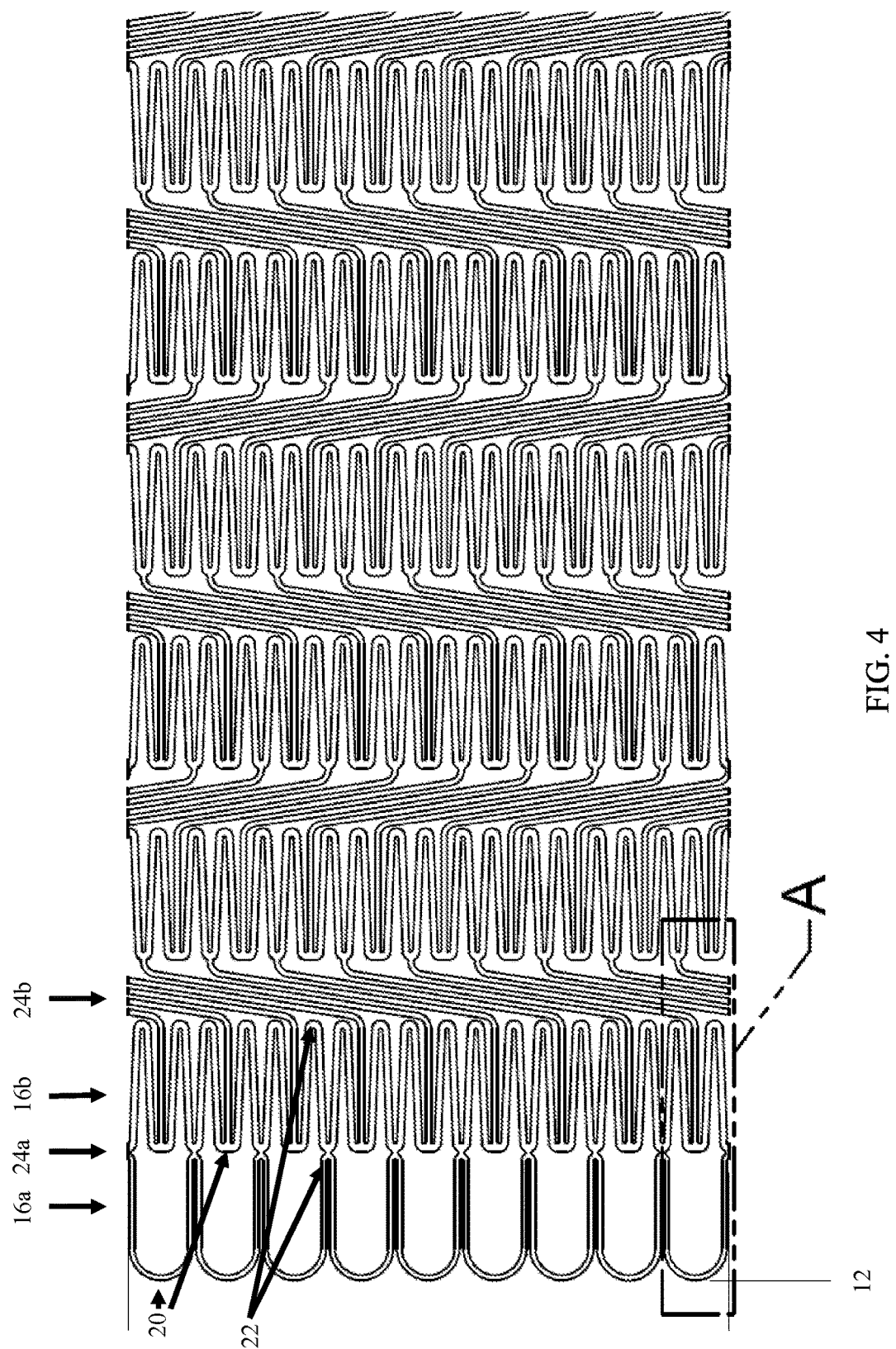
FIG. 4 is an enlargement of a portion of the stent pattern of FIG. 2.
Figure 5:
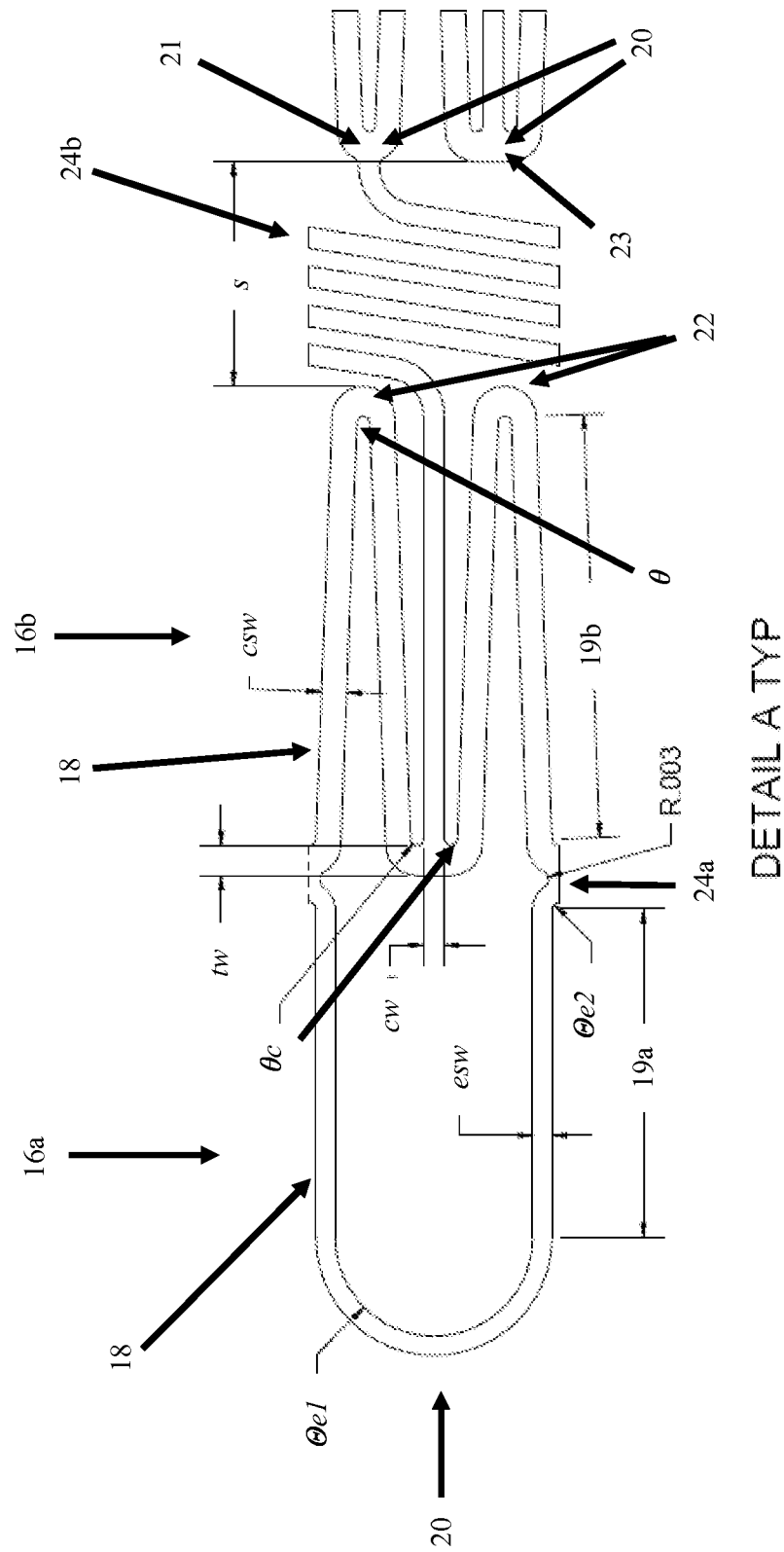
FIG. 5 is an enlargement of a portion of the stent pattern of FIG. 4.
Figure 6:
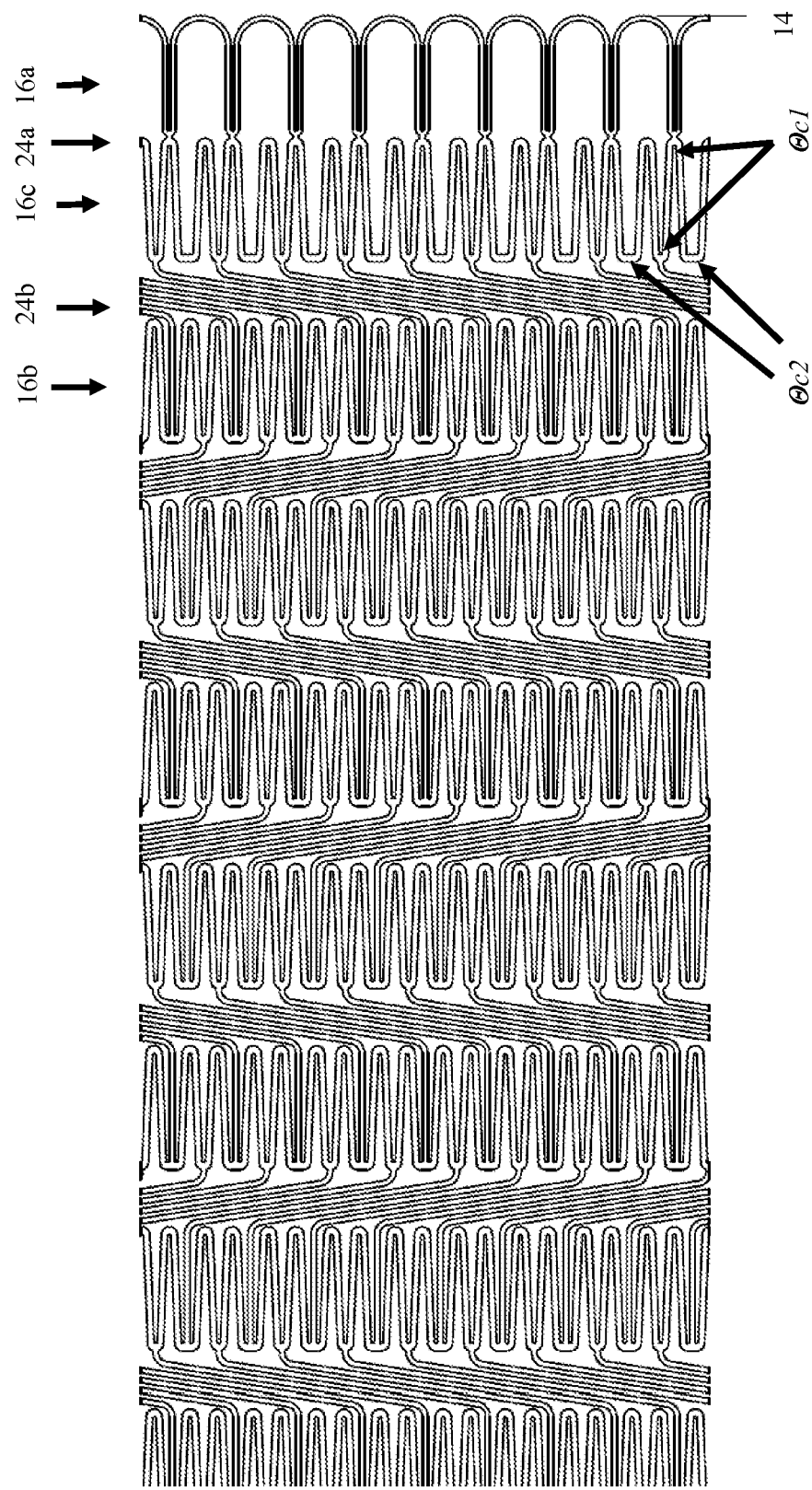
FIG. 6 is an enlargement of a portion of the stent pattern of FIG. 2.

As used in this disclosure, the "strut angle" $\theta$ is the angle between a pair of interconnected circumferentially adjacent members (e.g. struts 18, connectors 24). A pair of interconnected circumferentially adjacent members can be formed by two struts of a serpentine band, or by one strut of a serpentine band and a connector extending from the serpentine band. For a strut pair formed by two struts of a serpentine band, the strut angle $\theta$ is the angle between the two struts. A strut angle $\theta$ between two struts of a serpentine band is also the angle of the turn 20, 22 connecting the two struts. For a strut pair formed by one strut and a connector, the strut angle $\theta$ is the angle between the strut and the connector. For this type of strut angle $\theta$, the strut angle $\theta$ is smaller than the angle of the turn 20, 22 since the connector 24 is engaged to the turn 20, 22 (e.g. FIG. 4). Serpentine band 16b is an example of a serpentine band that has a strut angle $\theta$ between two struts 18 of the serpentine band, and a strut angle $\theta$ between one strut 18 and a connector 24b (e.g. FIGS. 2 and 4-5). Without being bound by theory, more force is needed to expand struts positioned farther apart than for struts positioned closer together. Thus, a pair of circumferentially adjacent members with a smaller strut angle expands a greater amount as compared to a pair of circumferentially adjacent members with a larger strut angle.

A serpentine band can have a uniform strut angle $\theta$, or a variable strut angle $\theta$. For example, serpentine bands 16a and 16c shown in FIGS. 2 and 4-5 have a variable strut angle $\theta$, while the serpentine bands 16a-j shown in FIG. 1 and the serpentine band 16b shown in FIGS. 2 and 4-5 have a uniform strut angle $\theta$. For serpentine band 16b, the strut angle $\theta$ between two struts 18 of the serpentine band 16b is equal to the strut angle $\theta$ between strut 18 and connector 24. For serpentine bands 16a, the proximal turns 20 have a greater strut angle $\theta$ than distal turns 22 and for serpentine band 16c, some of the proximal turns 20 either have a first strut angle $\theta$ or a second strut angle $\theta$, less than the first strut angle $\theta$ (e.g. FIG. 2).

Figure 3:
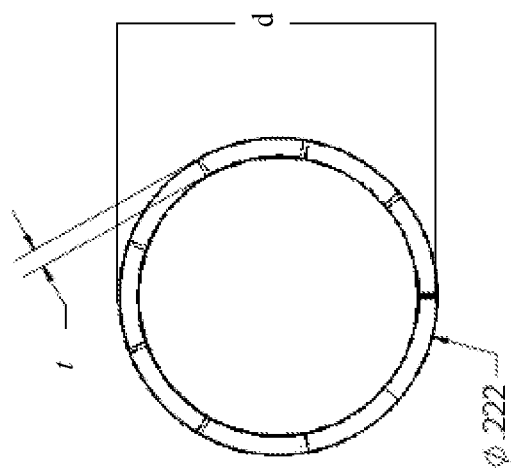
FIG. 3 is an end view of the stent of FIG. 2 is tubular form.

As used in this disclosure, the "wall thickness" t is measured radially from an inside surface of the stent to an outside surface of the stent (see e.g., FIG. 3). Since serpentine bands with thinner struts are weaker and have less resistance to radial collapse than serpentine bands with wider struts, providing serpentine bands with thinner struts at the ends of the stent decreases the radial force of the stent ends.

As used in this disclosure, a "strut pair" is a unit of a serpentine band consisting of two struts engaged by a turn, where a strut belongs to only one strut pair (in other words two circumferentially adjacent strut pairs do not share a strut in common). Since a turn is engaged to two struts, if a serpentine band has eight proximal turns, then the serpentine band has eight strut pairs. Because a serpentine band with fewer strut pairs is weaker and less resistant to radial collapse than a serpentine band with more strut pairs, providing serpentine bands with fewer strut pairs in the end regions, or at the ends, of the stent decreases the radial force of the stent end regions or stent ends. A serpentine band can have any number of strut pairs.

Thus, a stent of the present disclosure has serpentine bands that: increase in strut angle $\theta$ from each stent end to the stent center; increase in wall thickness t from each stent end to the stent center; increase in the number of strut pairs to the stent center; and combinations thereof. In at least one embodiment, the strut angle $\theta$ in a lower radial force region (e.g. a serpentine end band) is about five (5) to fifteen (15) times greater than the strut angle $\theta$ in a greater radial force region (e.g. a serpentine center band); the number of strut pairs in a greater radial force region (e.g. a serpentine center band) is 1.5 to 2 times the number of strut pairs in a serpentine band of a lower radial force region (e.g. a serpentine end band); and the wall thickness in a greater force region (e.g. a serpentine center band) is about 1.5 to 4 times greater than the wall thickness in a lower force region (e.g. a serpentine end band); and combinations thereof.

In one aspect, the increases in strut angle $\theta$, wall thickness t, and number of strut pairs from the stent end to the stent center is gradual. In other words, for a given stent pattern the strut angles $\theta$, the wall thickness t, and/or the number of strut pairs of the serpentine bands of a stent can be modified so that the difference in radial force is gradual. Thus, the serpentine bands of the stent have different strut angles θ, wall thicknesses t, and numbers of strut pairs. For example, a stent formed of serpentine bands 16a, 16c, 16e, 16g, 16i of FIG. 1 would have a radial force that gradually decreases from serpentine band 16e to serpentine band 16a, and from serpentine band 16e to serpentine band 16j.

In another aspect, only the transition region(s) of the stent has a gradual change in radial force. For example, the stent can have a center region with a first radial force, two end regions with a second radial force less than the first radial force, and one or two transition regions where a radial force tapers from the first radial force to the second radial force. Thus, in this embodiment, if the transition region(s) has a plurality of serpentine bands, the serpentine transition bands have different radial forces due to different strut angles θ, different wall thicknesses t, and different numbers of strut pairs; while the serpentine center bands have a uniform strut angle θ, a uniform wall thickness t, and a uniform number of strut pairs, and the serpentine end bands have a uniform strut angle θ, a uniform wall thickness t, and a uniform number of strut pairs. An example of a transition region with a gradual change in radial force would be a transition region comprising for example serpentine bands 16e, 16d, and 16b of FIG. 1.

In an alternate aspect, the serpentine bands of a region of the stent have a uniform strut angle θ, a uniform wall thickness t, and a uniform number of strut pairs. In other words, the serpentine center bands have a uniform strut angle θ, a uniform wall thickness t, and a uniform number of strut pairs, and the serpentine end bands have a uniform strut angle θ, a uniform wall thickness t, and a uniform number of strut pairs different than the serpentine center bands. For example, in FIG. 1, serpentine center bands 16e and 16f have a uniform strut angle θ, a uniform wall thickness t, and a uniform number of strut pairs and serpentine end bands 16a and 16b have a uniform strut angle θ, a uniform wall thickness t, and a uniform number of strut pairs different than the serpentine center bands. Further, if the stent includes a transition region, the serpentine transition bands have a uniform strut angle θ, a uniform wall thickness t, and a uniform number of strut pairs less than the serpentine center bands and greater than the serpentine end bands. This is also shown for example in FIG. 1 where serpentine bands 16c and 16d have a uniform strut angle θ, a uniform wall thickness t, and a uniform number of strut pairs that is less than the serpentine center bands 16e, 16f and greater than the serpentine end bands 16a 16b.

The stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, copolymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stents may be made of materials with shape memory effect, such as Nitinol; may be made of materials with superelastic properties, such as Nitinol; or may be made of materials which are plastically deformable. In the case of materials with shape memory effect, the stents may be provided with a memorized shape and then deformed to a reduced diameter shape. The stent may restore itself to its memorized shape upon being heated to a transition temperature and having any restraints removed therefrom.

The stents may be created by methods including cutting or etching a design from a tubular stock, from a flat sheet which is cut or etched and which is subsequently rolled. Any other suitable technique which is known in the art or which is subsequently developed may also be used to manufacture the stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Examples of stents exemplifying aspects discussed above are provided. A stent with variable radial force as discussed above is not limited to these specific examples. Some of these examples were referenced above as exemplifications of the general concepts discussed.

Example 1

One example of a stent with variable radial force along the longitudinal length as discussed above is shown in FIG. 1. In this example, the variable radial force of the stent is due to the serpentine bands 16 having an increase in strut angle θ from each stent end 12, 14 towards the center region; an increase in wall thickness t from each stent end 12, 14 towards the center region; and an increase in the number of strut pairs towards the center region.

In this example, the stent 10 has a first end region formed by serpentine end bands 16a and 16b; a first transition region formed by serpentine transition bands 16c and 16d; a center region formed by serpentine center bands 16e and 16f; a second transition region formed by serpentine transition bands 16g and 16h; and a second end region formed by serpentine end bands 16i and 16j. Although in this example each region has two serpentine bands, as discussed above each region can have one serpentine band, or a plurality of serpentine bands.

In this example, the serpentine end bands 16a, 16b, 16i, and 16j have fewer strut pairs than the serpentine transition bands 16c, 16d, 16g, and 16h; and the serpentine transition bands 16c, 16d, 16g, and 16h have fewer strut pairs than the serpentine center bands 16e and 16f. Specifically, in this example, each serpentine end band 16a, 16b, 16i, and 16j has four strut pairs; each serpentine transition band 16c, 16d, 16g, and 16h has six strut pairs; and each serpentine center band 16e and 16f has eight strut pairs. Thus, in this example, each serpentine band of a region of the stent has a uniform number of strut pairs.

In this example, the serpentine end bands 16a, 16b, 16i, and 16j have larger strut angle θ than the strut angle θ of the serpentine transition bands 16c, 16d, 16g, and 16h; and the serpentine transition bands 16c, 16d, 16g, and 16h have a larger strut angle θ than the strut angle θ of the serpentine center bands 16e and 16f. In this example, each serpentine band of a region of the stent has a uniform strut angle θ.

In this example, the thickness of the serpentine center bands is greater than the thickness of the serpentine transition bands, and the thickness of the serpentine transition bands is greater than the thickness of the serpentine end bands (not shown in the flat view of FIG. 1). In this aspect, each serpentine band of a region of the stent has a uniform thickness.

In this example, the serpentine bands 16 comprise straight struts 18. Also as shown, the struts of the serpentine end bands 16a, 16b, 16i, 16j have a uniform length that is smaller than a uniform length of struts of serpentine center bands 16e, 16f. Also the struts of serpentine transition bands 16c, 16d, 16g, 16h have a uniform length that is greater than the uniform length of the struts of the serpentine end bands 16a, 16b, 16i, 16j, and less than the uniform length of the strut of the serpentine center bands 16e, 16f.

In this example, the connectors 24 engage turns 20, 22 that face in opposite directions. As can be seen in FIG. 1, some of the connectors 24 extend longitudinally while others of the connector 24 extend circumferentially (e.g. ends of the connector are circumferentially offset).

Example 2

Another example of a stent with variable radial force along the longitudinal length as discussed above is shown in FIGS. 2-7. It is noted that FIGS. 2-7 show the stent in the unexpanded state. The stent 10 has a center region with a greater radial force than the end regions. In this example, the greater radial force is due to the serpentine center bands 16b, 16c having a greater number of strut pairs than the serpentine end bands 16a.

The center region of the stent 10 has a plurality of serpentine center bands 16b, 16c. In this example, the center region has fourteen serpentine center bands with a plurality of first serpentine center bands 16b and one second serpentine center band 16c.

Each serpentine center band 16b, 16c comprises center struts 18 interconnected by proximal turns 20 facing towards the proximal stent end 12 and distal turns 22 facing towards the distal stent end 14. Each center strut 18 has a center strut length 19b and a center strut width csw. In this example, the center strut length 19b is 0.1320 mm and the center strut width csw is 0.0078 mm (e.g. FIG. 5). In this example, each center strut is straight and at an oblique angle relative to the longitudinal axis of the stent. In this example, the proximal turns 20 include proximal turns 20 having a first circumferential extent 23 that is greater than the second circumferential extent 21 of other proximal turns 20 (e.g. FIGS. 2, 4, and 6). The distal turns 22 each have the second circumferential extent 21 (e.g. FIGS. 2, 4, and 6). In a further aspect, the turns 20, 22 have a turn width tw that is greater than the center strut width csw. In one embodiment, the turn width tw of the turns 20, 22 is 0.0094 mm. Adjacent serpentine center bands are circumferentially offset from one another, as can be observed by the proximal turns 20 having a first circumferential extent 23 of adjacent serpentine center bands having different circumferential positions. Adjacent serpentine center bands are spaced apart from one another by a spacing s (e.g. FIG. 5). In this example, the spacing s between adjacent serpentine center bands 16b, 16c is 0.070 mm.

The serpentine center bands 16b have a uniform number of strut pairs, a uniform strut angle θc, and a uniform wall thickness t. In this example, the serpentine center bands 16b have eighteen strut pairs; and a strut angle θc of 0.12 degrees between two struts of the serpentine center band 16b, and between one strut of the serpentine center band 16b and a connector 24b.

The serpentine center band 16c has the same number of strut pairs and same wall thickness t as the serpentine center bands 16b. However, in this example, the serpentine center band 16c has two different strut angles θc1 and θc2 as opposed to the uniform strut angle θc of serpentine center bands 16b because, in contrast to the serpentine center bands 16b, the serpentine center band 16c does not have any strut angles θ between one strut of the serpentine band 16b and one connector 24b (e.g. FIGS. 2 and 6). In this example, the first strut angle θc1 of serpentine center band 16c is equal to the strut angle θc (0.12 degrees) of serpentine center bands 16b, and the second strut angle θc2 of serpentine center band 16c is greater than the strut angle θc (0.12 degrees) of serpentine center bands 16b, and less than the strut angle θe (1.76 degrees) of serpentine end bands 16b.

Each end region of the stent 10 has one serpentine end band 16a. In this example, each serpentine end band is formed of end struts 18 interconnected by proximal turns 20 facing towards the proximal stent end 12 and distal turns 22 facing towards the distal stent end 14. Each end strut 18 has an end strut length 19a and an end strut width esw. In this example, the end strut length 19a is 0.1020 mm and the end strut width esw is 0.0060 mm (e.g. FIG. 5). In this example, the serpentine end band at the proximal stent end 12 (the proximal serpentine end band) has: a first strut angle θe1 between end struts connected to a proximal turn 20; a second strut angle θe2 between end struts connected to a distal turn 22; and two end struts connected to a proximal turn 20 are spaced farther apart than two end struts connected to a distal turn 22 (e.g. FIG. 4). Similarly, the serpentine end band at the distal stent end 14 (the distal serpentine end band) in this example has: a first strut angle θe1 between end struts connected to a distal turn 22; a second strut angle θe2 between end struts connected to a proximal turn 20; and two end struts connected to a distal turn 22 are spaced farther apart than two end struts connected to a proximal turn 20 (e.g. FIG. 6). Thus, each end strut is positioned a first circumferential distance from one circumferentially adjacent strut and a second circumferential distance from another circumferentially adjacent end strut where the first distance is larger than the second distance (e.g. FIGS. 4 and 6). In addition, each end strut is straight, and parallel to the longitudinal axis in this example.

In this example, the serpentine end bands 16a have a uniform number of strut pairs, the same two strut angles θe1 and θe2, and a uniform wall thickness t. As compared to the serpentine center bands 16b, the serpentine end bands 16a have fewer strut pairs and a smaller wall thickness t. In this example, the serpentine end bands 16a have nine strut pairs, a first strut angle θe1 of 1.76 degrees, and a second strut angle θe2 of 0.12 degrees.

Connectors 24 engage adjacent serpentine bands 16. In this example, the connectors 24 include longitudinal connectors 24a, and circumferential connectors 24b.

The longitudinal connectors 24a engage the end regions to the center region. In this example, the longitudinal connectors 24 are short and straight. A plurality of longitudinal connectors 24a engages a serpentine end band to a serpentine center band. In this example, each distal turn 22 of the proximal serpentine end band 16a is engaged to a proximal turn 20 of serpentine center band 16b by a longitudinal connector, and each proximal turn 20 of the distal serpentine end band 16a is engaged to a distal turn 22 of serpentine center band 16c (e.g. FIGS. 4 and 6). In this example, the longitudinal connectors are only engaged to turns 20, 22 having the second circumferential extent 21.

The circumferential connectors 24b engage adjacent serpentine center bands 16b, 16c. In this example, the circumferential connectors 24b are long and curvilinear. Also in this example, the circumferential connectors are narrower than the center struts. The circumferential connectors in this example have a width cw of 0.0065 mm (e.g. FIG. 5). Adjacent pairs of serpentine center bands are engaged by a plurality of circumferential connectors 24b. In this example, each circumferential connector 24b engages a proximal turn 20 having the first circumferential extent 23 and a proximal turn 20 having the second circumferential extent 21 (e.g. FIG. 7). In this example, the circumferential connector 24b has a straight longitudinal segment 26 extending from the proximal connector end 25 engaged to a proximal turn 20 having the first circumferential extent 23; a first curved segment 28 extending from the straight longitudinal segment 26; a straight circumferential segment 30 extending from the first curved segment 28; and a second curved segment 32 extending from the straight circumferential segment 30 to the distal connector end 33 engaged to a proximal turn 20 having a second circumferential extent 21 (e.g. FIG. 7). The straight longitudinal segment 26 of the circumferential connector 24b is positioned between two center struts (e.g. FIGS. 2 and 4-6). The circumferential segment 30 and the second curved segment 32 of the circumferential connector 24b are positioned in the spacing s between the two adjacent serpentine center bands. The circumferential segment 30 extends at an oblique angle relative to the longitudinal axis of the stent (e.g. FIG. 7). The ends 25, 33 of the circumferential connector 24b are circumferentially offset with the straight circumferential segment 30 being positioned between eight (8) pairs of turns 20, 22 and engaged to the proximal turn 20 of the ninth (9) pair of turns 20, 22 where a pair of turns is formed of a distal turn 22 of one serpentine center band and a proximal turn 20 of the adjacent serpentine center band (e.g. FIG. 7).

Figure 7:
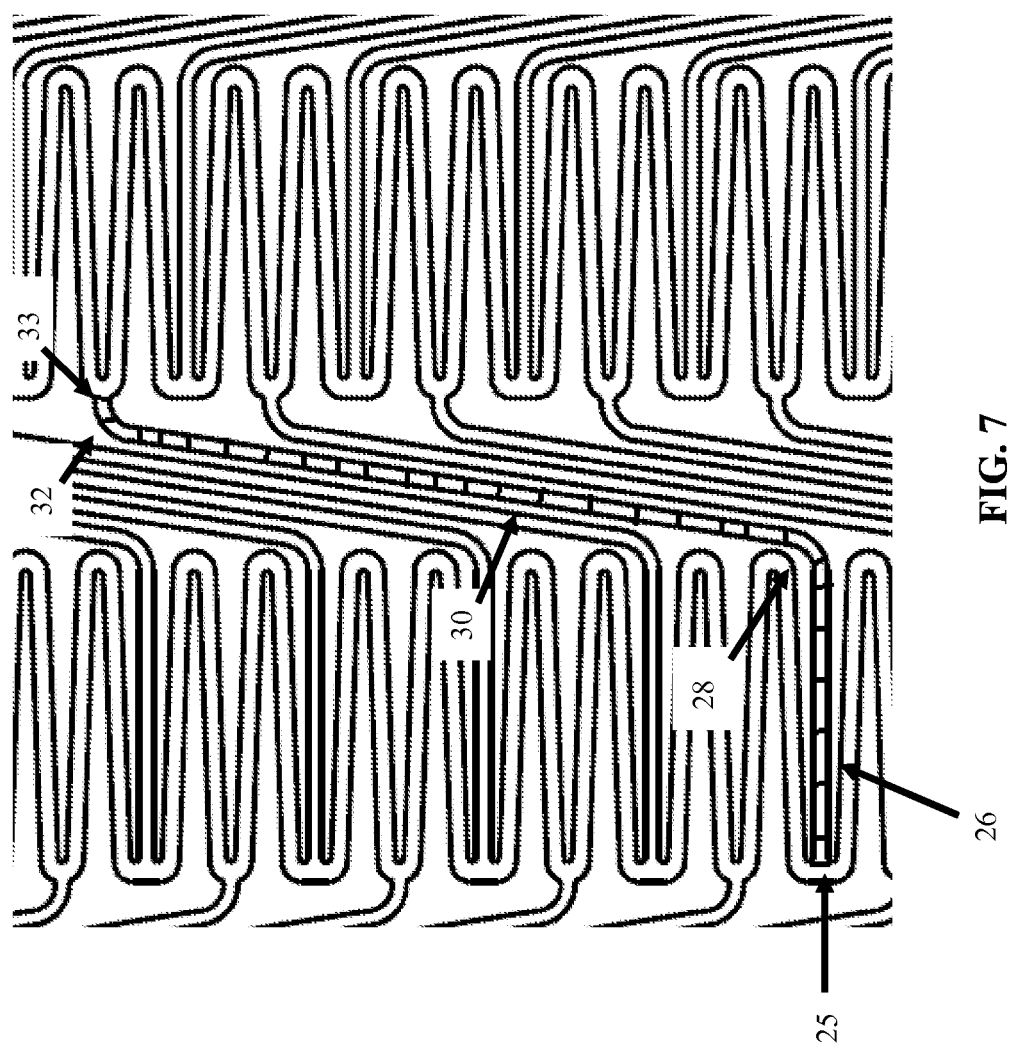
FIG. 7 is an enlargement of a portion of the stent pattern of FIG. 2.

In this example, the proximal turns 20 of a serpentine center band are either connected to the proximal connector end 25 or to the distal connector end 33 of a circumferential connector 24b, with the connectivity alternating between the proximal connector end 25 and the distal connector end 33 (e.g. FIG. 7). In a further aspect, the orientation of the first curved segment 28 of the circumferential connectors 24b alternates between two opposite orientations (e.g. FIGS. 2, 4, and 6). Thus although the orientation of the circumferential connectors 24b engaging two serpentine center bands is the same, the orientation of the circumferential connectors 24b between adjacent serpentine center bands 16b, 16c alternates along the longitudinal length of the stent (e.g. FIG. 2). Between two adjacent serpentine center bands, at any point around the circumference, four or five of the circumferential connectors 24b are positioned side-by-side and parallel to one another. In other words, a longitudinal line extending from one serpentine center band to the adjacent serpentine center band would cross four or five circumferential connectors 24b, depending on the circumferential position of the longitudinal line.

In a further aspect, at least the circumferential segment 30 extends outward from a stent envelope defined by the outer surface of the serpentine center bands when the stent is in a true expanded state. As used herein a "true expanded state" of the stent is when no force is being applied to radially contract the stent. The length of the circumferential segment affects the distance the circumferential connector extends outward from the stent envelope. Without being bound by theory, the height of the connector is correlated to radial force of the connector. For example, for two circumferential connectors that extend outward from the stent envelope for two different distances, the circumferential connector that extends outward for the greater distance has a lower radial force than a circumferential connector that extends outward for a smaller distance.

ADDITIONAL EXAMPLES

The following are additional examples of a stent with a variable radial force as disclosed above:

Example 1

A stent having a stent envelope and a longitudinal axis, the stent comprising:
 a plurality of members, the plurality of members comprising struts and connectors, the struts interconnected by turns to form serpentine bands, the serpentine bands being interconnected;
 the serpentine bands including:
  two end bands, each end band formed by a first number of struts, the struts of the end bands extending parallel to the longitudinal axis of the stent, the turns of each end band including end turns that form an end of the stent and inner turns, struts engaged to an end turn being spaced a first circumferential distance apart and struts engaged to an inner turn being spaced a second circumferential distance apart that is less than the first circumferential distance; and
  a plurality of center bands, each center band formed by a second number of struts less than the first number of struts, the struts of the center bands extending at a non-parallel angle to the longitudinal axis of the stent, adjacent middle bands being interconnected by first connectors;
 wherein each first connector has a circumferential connector segment that extends outward from the stent envelope when the stent is in the expanded state.

Example 2

The stent of example 1, wherein the turns of each center band include:

proximal turns, each proximal turn engaged only to two struts and one first connector; and
distal turns, each distal turn engaged to only two struts.

Example 3

The stent of any one of examples 1-2, wherein the circumferential connector segment is positioned between two adjacent center bands.

Example 4

The stent of any one of examples 1-3, wherein each first connector further has a longitudinal connector segment positioned between two struts of a center band, and a first curved connector segment engaging the longitudinal connector segment to the circumferential connector segment, the longitudinal connector segment engaged to a proximal turn.

Example 5

The stent of example 4, wherein a strut angle between the longitudinal connector segment and each of the two struts of the center band is uniform.

Example 6

The stent of any one of examples 4-5, wherein each first connector further has a second curved connector segment engaged to a proximal turn of an adjacent center band.

Example 7

The stent of example 6, the center bands including two first center bands, each first center band engaged to an end band by longitudinal connectors.

Example 8

The stent of any one of examples 1-7, each end band having a first number of struts and each center band having a second number of struts.

Example 9

The stent of any one of examples 1-8, wherein the center bands have a greater radial force than the end bands, wherein the center bands have a greater number of strut pairs as compared to the end bands.

Example 10

The stent of example 9, wherein the center band further have a greater thickness as compared to the end bands.

Example 11

The stent of any one of examples 9-10, wherein the center band further has a smaller strut angle than the end bands.

Example 12

A stent having a longitudinal length, a radial force that varies along the longitudinal length, and a plurality of serpentine bands forming a center region and two end regions, each serpentine band comprising struts interconnected by proximal turns and distal turns, wherein the center region of the stent has a greater radial force than end regions of the stent, the center region and the end regions each having a strut angle, a number of strut pairs, and a wall thickness, wherein:
the strut angle of the center region is less than the strut angle of the end regions;
the number of strut pairs of the center region is greater than the number of strut pairs of the end regions; and
the wall thickness of the center region is greater than the wall thickness of the end regions.

Example 13

The stent of example 12, the plurality of serpentine bands further forming a transition region positioned between the center region and each end region, the transition region having a strut angle, a number of strut pairs, and a wall thickness, wherein:
the strut angle of the transition region is greater than the strut angle of the center region and less than the strut angle of the end regions;
the number of strut pairs is less than the number of strut pairs of the center region and greater than the number of strut pairs of the end regions; and
the wall thickness is less than the wall thickness of the center region, and greater than the wall thickness of the end regions.

Example 14

The stent of example 12, the plurality of serpentine bands further forming a transition region positioned between the center region and each end region, the transition region having a variable strut angle, a variable number of strut pairs, and a variable wall thickness, wherein:
the variable strut angle decreases from the center region to the end region,
the variable number of strut pairs decreases from the center region to the end region, and
the variable wall thickness decreases from the center region to the end region.

Example 15

The stent of any one of examples 12 to 14, the plurality of serpentine bands comprising:
serpentine center bands forming the center region, and
serpentine end bands, one serpentine end band forming each end region.

Example 16

The stent of example 15, wherein for each serpentine center band:
the number of strut pairs is 1.5 to 2 times the number of strut pairs of the serpentine end bands;
the strut angle is about 5 to 15 times larger than the strut angle of the serpentine end bands; and
the wall thickness is about 1.5 to 4 times larger than the wall thickness of the serpentine end bands.

Example 17

The stent of example 16, further wherein for each serpentine center band:
a strut length is greater than a strut length of the serpentine end bands; and a strut width is greater than a strut width of the serpentine end bands.

Example 18

The stent of example 15, wherein each serpentine end band is engaged to a serpentine center band by longitudinal connectors and adjacent serpentine center bands are engaged by circumferential connectors.

Example 19

The stent of example 18, wherein an orientation of the circumferential connectors alternates between two opposite orientations along the longitudinal length of the stent.

Example 20

The stent of example 18, wherein each longitudinal connector engages one proximal turn and one distal turn, and each circumferential connector engages two proximal turns.

Example 21

The stent of example 20, the one serpentine end band forming each end region being a proximal serpentine end band and a distal serpentine end band, each distal turn of a proximal serpentine end band is engaged to a proximal turn of a serpentine center band by a longitudinal connector and each proximal turn of a distal serpentine end band is engaged to a distal turn of a serpentine center band by a longitudinal connector.

Example 22

The stent of example 20, each circumferential connector comprising a straight longitudinal segment, a first curved segment, a circumferential segment, and a second curved segment.

Example 23

A stent having a stent envelope and a longitudinal axis, the stent comprising:
a center region, the center region comprising interconnected serpentine center bands, each center band formed by center struts extending at a non-parallel angle to the longitudinal axis of the stent, each serpentine center band comprising a first number of strut pairs, adjacent center bands being interconnected by circumferential connectors;
two end regions, each end region comprising a serpentine end band, each end band formed by end struts extending parallel to the longitudinal axis of the stent, each serpentine end band comprising a second number of strut pairs less than the first number, each end region engaged to the center region by a longitudinal connector;

Example 24

A stent having a stent envelope and a longitudinal axis, the stent comprising:
a center region, the center region comprising serpentine center bands, each center band formed by center struts extending at a non-parallel angle to the longitudinal axis of the stent, adjacent center bands being interconnected by circumferential connectors, the center bands including first center bands and one second center band, each first center band having a uniform strut angle and the second center band having a first strut angle and a second strut angle greater than the first strut angle;
two end regions, each end region comprising a serpentine end band, each end band formed by end struts extending parallel to the longitudinal axis of the stent, the end struts interconnected by turns, each turn engaged to two end struts, the turns comprising proximal turns and distal turns, end struts engaged to a proximal turn having a greater strut angle than end struts engaged to a distal turn, each end region engaged to the center region by a longitudinal connector;

Example 25

The stent of example 24, the uniform strut angle of the first center band including strut angles between two center struts and strut angles between one center strut and one circumferential connector.

Example 26

A stent having a longitudinal length, a radial force that varies along the longitudinal length, and interconnected serpentine bands, each serpentine band comprising struts interconnected by proximal turns and distal turns, each serpentine band having a strut angle, a number of strut pairs, and a wall thickness, the serpentine bands comprising a first serpentine band having a first radial force and a second serpentine band having a second radial force less than the first radial force, wherein:
the strut angle of the first serpentine band is less than the strut angle of the second serpentine band;
the number of strut pairs of the first serpentine band is greater than the number of strut pairs of second serpentine band; and
the wall thickness of the first serpentine band is greater than the wall thickness of the second serpentine band.

Example 27

The stent of example 26, wherein the first serpentine band is positioned between two second serpentine bands, each second serpentine band forming an end of the stent, the radial force gradually decreasing from the first radial force of the first serpentine band to the second radial force of the second serpentine bands at each end of the stent.

Example 28

The stent of example 26, wherein the first serpentine bands are a plurality of serpentine bands forming a center region of the stent, and the second serpentine bands are a plurality of serpentine bands forming a first end region and a second end region of the stent, the center region being positioned between the first and second end regions, the first and second end regions having a lower radial force than the center region.

Example 29

The stent of any one of examples 26-28, the serpentine bands further comprising a third serpentine band positioned between the first and second serpentine bands, the third serpentine band having a third radial force less than the first radial force and greater than the second radial force, wherein:

the strut angle of the third serpentine band is greater than the strut angle of the first serpentine band and less than the strut angle of the second serpentine band;

the number of strut pairs of the third serpentine band is less than the number of strut pairs of the first serpentine band and greater than the number of strut pairs of the first serpentine band; and the wall thickness of the third serpentine band is less than the wall thickness of the first serpentine band, and greater than the wall thickness of the second serpentine band.

Example 30

The stent of example 29, the third serpentine band being a plurality of third serpentine bands forming transition regions positioned between the center region and each end region, wherein for the third serpentine bands:

the strut angle decreases from the center region to the end region, the number of strut pairs decreases from the center region to the end region, and the wall thickness decreases from the center region to the end region.

Example 31

The stent of any one of examples 26-30, wherein for the first serpentine band:

the strut angle is about 5 to 15 times smaller than the strut angle of the second serpentine band;

the number of strut pairs is 1.5 to 2 times the number of strut pairs of the second serpentine band; and the wall thickness is about 1.5 to 4 times larger than the wall thickness of the second serpentine band.

Example 32

The stent of any one of examples 26-31, the struts having a strut length and a strut width, further wherein for the first serpentine band:

the strut length is greater than the strut length of the second serpentine band; and the strut width is greater than the strut width of the second serpentine band.

Example 33

The stent of claim any one of examples 28 and 31-32, wherein each second serpentine band is engaged to a first serpentine band by longitudinal connectors and adjacent first serpentine bands are engaged by circumferential connectors.

Example 34

The stent of example 33, wherein each longitudinal connector engages one proximal turn and one distal turn, and each circumferential connector engages two proximal turns.

Example 35

The stent of any one of examples 33-34, each circumferential connector comprising a straight longitudinal segment, a first curved segment, a circumferential segment, and a second curved segment, the straight longitudinal segment positioned between two struts of a first serpentine band.

Example 36

The stent of any one of examples 33-35, wherein an orientation of the circumferential connectors engaging two serpentine center bands is the same but alternates between two opposite orientations along the longitudinal length of the stent.

Example 37

The stent of example 35, wherein the circumferential segment is configured to extend outward from a stent envelope defined by the first serpentine band when the stent is in a true expanded state.

Example 38

The stent of any one of examples 26-37, wherein the struts are straight.

Example 39

The stent of any one of examples 28-38, wherein the struts of the center region are at an angle relative to the longitudinal axis of the stent, and the struts of the end regions are parallel to the longitudinal axis of the stent.

Example 40

The stent of any one of examples 26-39, wherein each serpentine band has a uniform strut angle.

Example 41

A stent with a variable radial force comprising:

a first serpentine band comprising struts interconnected by proximal turns and distal turns, a first strut angle, a first number of strut pairs, and a first wall thickness; and a second serpentine band comprising struts interconnected by proximal turns and distal turns, a second strut angle less than the first strut angle, a second number of strut pairs greater than the first number of strut pairs, and a second wall thickness greater than the first wall thickness.

Example 42

The stent of example 41, the first serpentine band being two serpentine end bands, one of the two serpentine end bands forming one end of the stent and the other of the two serpentine end bands forming the other end of the stent, the second serpentine band being a plurality of serpentine center bands positioned between the two serpentine end bands.

Example 43

The stent of example 42, wherein one of the two serpentine end bands is engaged to one of the plurality of serpentine center bands by a first plurality of longitudinal connectors; and the other serpentine end band is engaged to another of the plurality of serpentine center bands by a second plurality of longitudinal connectors; and pairs of serpentine center bands being engaged by a plurality of circumferential connectors.

Example 44

The stent of example 41, wherein:

the second number of strut pairs is 1.5 to 2 times the first number of strut pairs;

the first strut angle is about 15 times larger than the second strut angle; and the first wall thickness is about 1.5 to 4 times greater than the second wall thickness.

Example 45

The stent of example 44, the struts of the first serpentine bands having a first strut length and a first strut width;
the struts of second serpentine bands having a second strut length and a second strut width;
wherein the second strut length is greater than the first strut length, and the second strut width is greater than the first strut width.

Example 46

A stent comprising:
a first serpentine end band forming a first end of the stent, and a second serpentine end band forming a second end of the stent, each serpentine end band comprising struts interconnected by proximal turns and distal turns, an end band number of strut pairs, an end band strut angle, and an end band thickness;
serpentine center bands comprising center struts interconnected by proximal turns and distal turns, a center band number of strut pairs greater than the end band number of strut pairs, a center band strut angle less than the end band strut angle, and a center band thickness greater than the end band thickness;
circumferential connectors engaging proximal turns of adjacent center serpentine bands;
a first plurality of longitudinal connectors engaging one of the center serpentine bands to the first serpentine end band; and
a second plurality of longitudinal connectors engaging another of the center serpentine bands to the second serpentine end band.

Example 47

The stent of example 46, each serpentine end band and each serpentine center band comprising proximal turns and distal turns, wherein each longitudinal connector engages one proximal turn and one distal turn, and each circumferential connector engages two proximal turns.

Example 48

The stent of any one of examples 46-47, wherein the end band number of strut pairs is nine strut pairs, and the end band strut angle is about 1.76 degrees; the end band thickness is about 0.0130 mm; the center band number of strut pairs is eighteen strut pairs, the center band strut angle is about 0.120 degrees; and the center band thickness is about 0.0130 mm.

Example 49

The stent of any one of examples 46-48, wherein the center struts are at an angle relative to the longitudinal axis of the stent, and the end struts are parallel to the longitudinal axis of the stent.

Example 50

The stent of any one of examples 46-49, wherein each end strut is positioned a first distance from one adjacent end strut and a second distance from another adjacent end strut, the second distance being greater than the first distance.

Example 51

The stent of any one of examples 16, 31, and 44 wherein for each serpentine center band:
the number of strut pairs is 1.5 times the number of strut pairs of the serpentine end bands;
the strut angle is about 5 times larger than the strut angle of the serpentine end bands;
the wall thickness is about 1.5 times larger than the wall thickness of the serpentine end bands.

Example 52

The stent of any one of examples 16, 31, and 44 wherein for each serpentine center band:
the number of strut pairs is 2 times the number of strut pairs of the serpentine end bands;
the strut angle is about 5 times larger than the strut angle of the serpentine end bands;
the wall thickness is about 1.5 times larger than the wall thickness of the serpentine end bands.

Example 53

The stent of any one of examples 16, 31, and 44 wherein for each serpentine center band:
the number of strut pairs is 1.5 times the number of strut pairs of the serpentine end bands;
the strut angle is about 10 times larger than the strut angle of the serpentine end bands;
the wall thickness is about 1.5 times larger than the wall thickness of the serpentine end bands.

Example 54

The stent of any one of examples 16, 31, and 44 wherein for each serpentine center band:
the number of strut pairs is 1.5 times the number of strut pairs of the serpentine end bands;
the strut angle is about 15 times larger than the strut angle of the serpentine end bands;
the wall thickness is about 1.5 time larger than the wall thickness of the serpentine end bands.

Example 55

The stent of any one of examples 16, 31, and 44 wherein for each serpentine center band:
the number of strut pairs is 1.5 times the number of strut pairs of the serpentine end bands;
the strut angle is about 15 times larger than the strut angle of the serpentine end bands;
the wall thickness is about 4 times larger than the wall thickness of the serpentine end bands.

Example 56

The stent of any one of examples 16, 31, and 44 wherein for each serpentine center band:
the number of strut pairs is 2 times the number of strut pairs of the serpentine end bands;
the strut angle is about 15 times larger than the strut angle of the serpentine end bands;

the wall thickness is about 4 times larger than the wall thickness of the serpentine end bands.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the present disclosure such that the present disclosure should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the present disclosure. Those skilled in the art may recognize other equivalents to the specific embodiment described herein which equivalents are intended to be encompassed by the claims attached hereto.

The invention claimed is:

1. A stent having a longitudinal length, a radial force that varies along the longitudinal length, and a plurality of interconnected serpentine bands, wherein each serpentine band comprises a number of strut pairs interconnected by proximal turns and distal turns, each serpentine band having a strut angle measured between the pairs of interconnected struts at the proximal or distal turns, and a wall thickness, the serpentine bands comprising a first serpentine band having a first radial force and a second serpentine band having a second radial force less than the first radial force, wherein:
the strut angle of the first serpentine band is less than the strut angle of the second serpentine band;
the number of strut pairs of the first serpentine band is greater than the number of strut pairs of second serpentine band; and
the wall thickness of the first serpentine band is greater than the wall thickness of the second serpentine band;
the struts having a strut length and a strut width measured along a straight portion of the strut between proximal and distal turns, further wherein for the first serpentine band:
the strut length is greater than the strut length of the second serpentine band; and
the strut width is greater than the strut width of the second serpentine band;
the serpentine bands further comprising a third serpentine band positioned between the first and second serpentine bands, the third serpentine band having a third radial force less than the first radial force and greater than the second radial force, wherein:
the strut angle of the third serpentine band is greater than the strut angle of the first serpentine band and less than the strut angle of the second serpentine band;
the number of strut pairs of the third serpentine band is less than the number of strut pairs of the first serpentine band and greater than the number of strut pairs of the first serpentine band; and
the wall thickness of the third serpentine band is less than the wall thickness of the first serpentine band, and greater than the wall thickness of the second serpentine band.

2. The stent of claim 1, wherein the first serpentine band is positioned between two second serpentine bands, each second serpentine band forming an end of the stent.

3. The stent of claim 1, wherein the first serpentine bands are a plurality of serpentine bands forming a center region of the stent, and the second serpentine bands are a plurality of serpentine bands forming a first end region and a second end region of the stent, the center region being positioned between the first and second end regions, the first and second end regions having a lower radial force than the center region, the center region being devoid of the second serpentine bands.

4. The stent of claim 3, wherein each second serpentine band is engaged to a first serpentine band by longitudinal connectors and adjacent first serpentine bands are engaged by circumferential connectors.

5. The stent of claim 4, wherein each longitudinal connector engages one proximal turn and one distal turn, and each circumferential connector engages two proximal turns.

6. The stent of claim 4, each circumferential connector comprising a straight longitudinal segment, a first curved segment, a circumferential segment, and a second curved segment, the straight longitudinal segment positioned between two struts of a first serpentine band.

7. The stent of claim 6, wherein an orientation of the circumferential connectors engaging two serpentine center bands is the same but alternates between two opposite orientations along the longitudinal length of the stent.

8. The stent of claim 1, the third serpentine band being a plurality of third serpentine bands forming transition regions positioned between a center region and opposing end regions.

9. A stent with a variable radial force comprising:
a first serpentine band comprising struts interconnected by proximal turns and distal turns, a first strut angle, a first number of strut pairs, and a first wall thickness, the first strut angle measured between interconnected struts at the proximal or distal turns of the first serpentine band; and
a second serpentine band comprising struts interconnected by proximal turns and distal turns, a second strut angle less than the first strut angle, a second number of strut pairs greater than the first number of strut pairs, and a second wall thickness greater than the first wall thickness, the second strut angle measured between interconnected struts at the proximal or distal turns of the second serpentine band;
wherein the second number of strut pairs is twice the first number of strut pairs;
wherein the first strut angle is 5 to 15 times larger than the second strut angle; and
wherein the first wall thickness is 1.5 to 4 times greater than the second wall thickness.

10. The stent of claim 9, the first serpentine band being two serpentine end bands, one of the two serpentine end bands forming one end of the stent and the other of the two serpentine end bands forming the other end of the stent, the second serpentine band being a plurality of serpentine center bands positioned between the two serpentine end bands.

11. The stent of claim 10, wherein one of the two serpentine end bands is engaged to one of the plurality of serpentine center bands by a first plurality of longitudinal connectors; and the other serpentine end band is engaged to another of the plurality of serpentine center bands by a second plurality of longitudinal connectors; and pairs of serpentine center bands being engaged by a plurality of circumferential connectors.

12. The stent of claim 9, the struts of the first serpentine bands having a first strut length and a first strut width;
the struts of second serpentine bands having a second strut length and a second strut width;
wherein the second strut length is greater than the first strut length, and the second strut width is greater than the first strut width.

13. A stent comprising:
a first serpentine end band forming a first end of the stent, and a second serpentine end band forming a second end of the stent, each serpentine end band comprising an end band number of strut pairs interconnected by proximal turns and distal turns, an end band strut angle measured between the pairs of interconnected end band struts at the proximal or distal turns, and an end band thickness, wherein a longitudinal axis of the stent extends from the first end of the stent to the second end of the stent;
a plurality of serpentine center bands comprising a center band number of strut pairs interconnected by proximal turns and distal turns, the center band number of strut pairs being greater than the end band number of strut pairs, a center band strut angle measured between the pairs of interconnected center band struts at the proximal or distal turns, the center band strut angle being less than the end band strut angle, and a center band thickness being greater than the end band thickness;
circumferential connectors engaging proximal turns of adjacent center serpentine bands, wherein the proximal turns of the adjacent center serpentine bands engaged by one of the circumferential connectors are offset circumferentially from each other by at least two proximal turns;
a first plurality of longitudinal connectors engaging one of the center serpentine bands to the first serpentine end band; and
a second plurality of longitudinal connectors engaging another of the center serpentine bands to the second serpentine end band;
wherein the center struts are at an angle relative to the longitudinal axis of the stent and the end struts are parallel to the longitudinal axis of the stent, wherein each end strut is positioned a first circumferential distance from one adjacent end strut and a second circumferential distance from another adjacent end strut, the second distance being greater than the first distance.

14. The stent of claim 13, each serpentine end band and each serpentine center band comprising proximal turns and distal turns, wherein each longitudinal connector engages one proximal turn and one distal turn, and each circumferential connector engages two proximal turns.

15. The stent of claim 13, wherein the end band number of strut pairs is nine strut pairs, and the end band strut angle is 1.76 degrees; the end band thickness is 0.0130 mm; the center band number is eighteen strut pairs, the center band strut angle is 0.120 degrees; and the center band thickness is 0.0130 mm.

16. The stent of claim 13, wherein the circumferential connectors extend circumferentially between eight pairs of turns, wherein each pair of turns is formed by a distal turn of one center serpentine band and a proximal turn of the adjacent center serpentine band.

17. The stent of claim 13, wherein a circumferential orientation of the circumferential connectors between adjacent center serpentine bands alternates along the longitudinal axis of the stent.

18. The stent of claim 13, wherein between two adjacent serpentine center bands, at any point around a circumference of the stent, four or five of the circumferential connectors are positioned side-by-side and parallel to one another.

* * * * *